United States Patent [19]

Henszey et al.

[11] Patent Number: 5,363,874

[45] Date of Patent: Nov. 15, 1994

[54] AUTOMATED SAMPLE CONDITIONING MODULE

[75] Inventors: Richard R. Henszey, Oconomowoc; Bruce Weiss, Whitefish Bay, both of Wis.

[73] Assignee: Sentry Equipment Corp., Oconomowoc, Wis.

[21] Appl. No.: 958,002

[22] Filed: Oct. 8, 1992

[51] Int. Cl.$^5$ ............................................. F16K 31/64
[52] U.S. Cl. ................................. 137/14; 137/487.5; 73/863.03; 73/863.11
[58] Field of Search ............... 137/487, 487.5, 14; 73/863.03, 863.11; 422/68.1, 81

[56] References Cited

U.S. PATENT DOCUMENTS

| | | | |
|---|---|---|---|
| 2,091,613 | 8/1937 | Polston | 73/21 |
| 3,062,055 | 11/1962 | Bills | 73/422 |
| 3,203,250 | 8/1965 | Coggeshall et al. | 73/422 |
| 3,469,591 | 9/1969 | Odendahl | 137/14 |
| 3,543,784 | 12/1970 | Smith | 137/487 X |
| 3,598,149 | 8/1971 | Witkin | 137/599 |
| 3,730,203 | 5/1973 | Katzer et al. | 137/14 |
| 3,776,249 | 12/1973 | Wailes et al. | 137/487.5 X |
| 3,871,444 | 3/1975 | Houser et al. | 165/101 |
| 3,875,955 | 4/1975 | Gallatin et al. | 137/487 X |
| 3,880,226 | 4/1975 | Houser et al. | 165/11 |
| 4,106,525 | 8/1978 | Currie et al. | 138/43 |
| 4,277,832 | 7/1981 | Wong | 137/487 X |
| 4,317,379 | 3/1982 | Oberlander et al. | 73/863.12 |
| 4,340,234 | 7/1982 | Ise | 137/513.3 X |
| 4,472,354 | 9/1984 | Passell et al. | 422/62 |
| 4,631,967 | 12/1986 | Welker | 73/861.25 |
| 4,713,772 | 12/1987 | Carlson | 364/496 |
| 4,766,550 | 8/1988 | Byers et al. | 364/497 |
| 4,796,651 | 1/1989 | Ginn et al. | 137/487 X |
| 4,877,051 | 10/1989 | Day | 137/487.5 X |
| 4,978,506 | 12/1990 | Calderwood | 422/73 |
| 5,005,432 | 4/1991 | Faulkner | 73/863.86 |
| 5,129,418 | 7/1992 | Shimomura et al. | 137/487.5 X |
| 5,146,941 | 9/1992 | Statler | 137/487.5 X |
| 5,152,309 | 10/1992 | Twerdochlib et al. | 137/487.5 X |

OTHER PUBLICATIONS

Sentry—"Single Line Sample Panel" Bulletin 1.37.1, Dated Sep. 1990.
Sentry—"Variable Pressure Reducing Element Model VREL" Bulletin 1.10.1, Dated Oct. 1987.

Primary Examiner—John Rivell
Attorney, Agent, or Firm—Nilles & Nilles

[57] ABSTRACT

An automated sample conditioning system for conditioning and preparing steam and hot water samples at a constant flow rate and velocity continuously monitors and adjusts flow rate in the sample line. Sample flow is metered through a flow rate device such as an orifice plate of known flow characteristics, and a downstream pressure value is provided by either a fixed back pressure regulator/relief valve or by a pipe section of known length and diameter. A pressure transducer continuously monitors pressure in the sample line upstream from the orifice plate. A control analyzer automatically adjusts a motorized pressure reducing device in response to fluctuations in pressure monitored by the pressure transducer in order to maintain constant flow rate and velocity. Monitoring devices and displays acquire, display and control critical pressure, temperature and flow rate parameters throughout the system. Network communications capability for remote, unattended monitoring control and data acquisition is also provided.

34 Claims, 5 Drawing Sheets

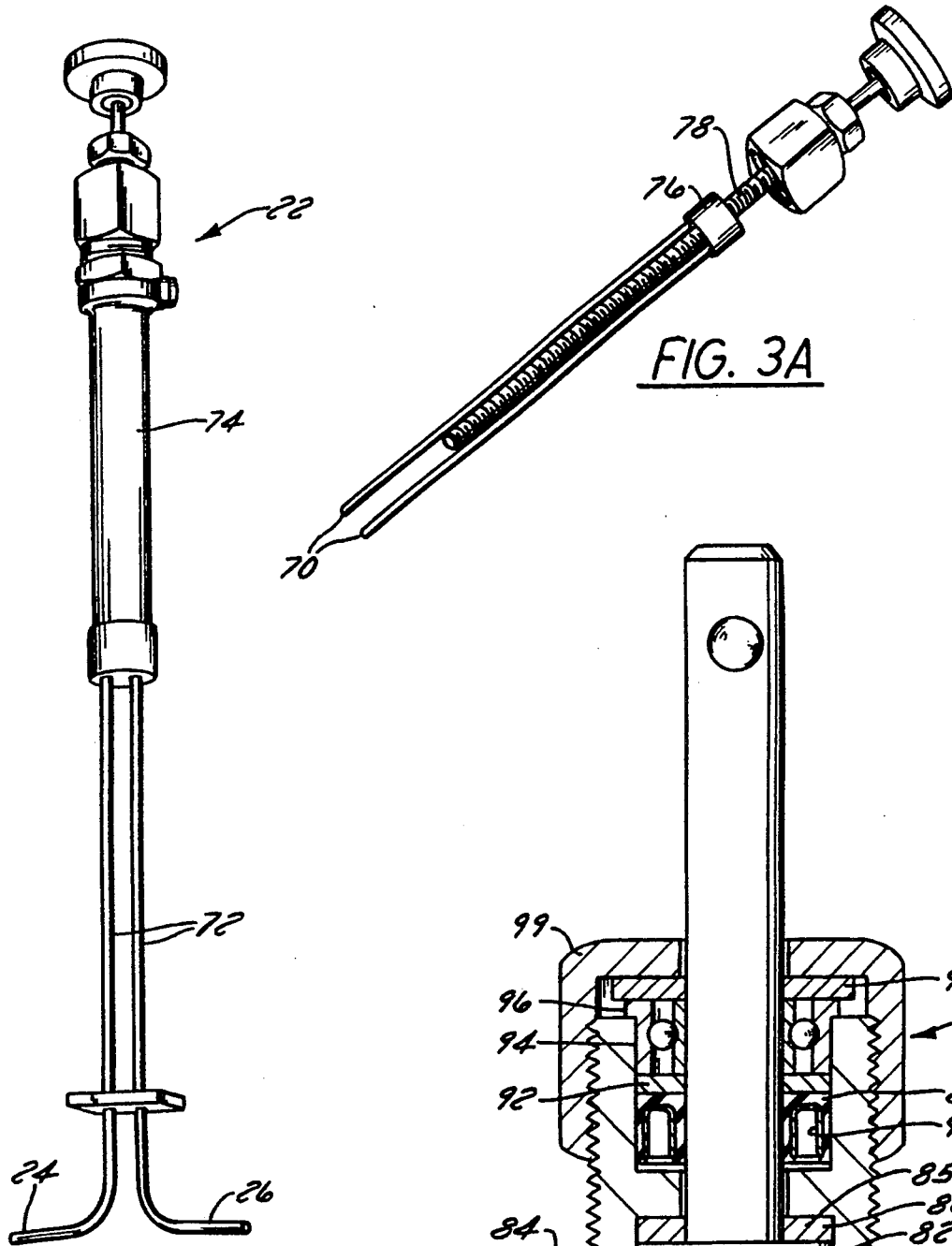

AUTOMATED SAMPLE CONDITIONING MODULE

BACKGROUND OF THE INVENTION

1. Field of the Invention

This invention relates to an automated sample conditioning module for condensing, cooling and reducing pressure of hot fluid samples. In particular, the invention relates to a system for conditioning steam and hot water samples at a constant sample flow rate and velocity, automatically adjustable at all varying source pressures, for preparing the sample for analysis.

2. Background of the Related Technology

An operator of a steam and hot water system at a utility power plant or other steam plant must carefully monitor and control water chemistry in the system. Common water impurities may cause corrosion, restricted water flow, fouling of heat exchange surfaces, mineral deposits and build-up of crud or scale, and a variety of other operating problems in a power plant. Successful operation of a power plant therefore requires frequent collection of steam and hot water samples which can be analyzed to provide useful information on the chemistry of the steam-water cycle.

A sample from a steam or water system must be carefully handled in order to assure that the sample is representative of conditions in the system. Analysis equipment is typically capable of measuring very small concentrations of contaminants in water, some equipment being capable of measuring in the parts per billion (ppb) range. On-line water chemistry instrumentation often includes analysis for pH, conductivity, dissolved oxygen, hydrazine, sodium, and chloride content. Unless the sample is representative of current conditions at the source, even the most sensitive analytical equipment is useless. Alteration of the properties of the sample during the sampling process can result from a number of causes, such as non-representative sample extraction, deposition or re-entrainment of solids, absorption or release of impurities, air leakage into the sample line, or contamination of the sample during handling.

This invention is concerned primarily with conditioning of the sample, namely, condensing, cooling, reducing pressure and controlling flow rate of the sample to prepare it for analysis.

Recently the need for continuous measurement of water chemistry parameters has been recognized in the power plant industry, which in turn requires the continuous extraction of a sample for analysis. The Electric Power Research Institute (EPRI) and several plant chemistry experts recommend a constant liquid sample velocity of about 6 feet per second at all varying source pressures. A study by EPRI showed that for most liquid sample analysis situations sampling at a linear velocity of 6 feet per second decreased the sample line loss of insoluables to a negligible amount, and it minimized the time required to establish equilibrium between the amount of particulate transferred to and from the sample line. (See *Guideline Manual on Instrumentation and Control for Fossil Plant Cycle Chemistry*, EPRI CS-5164, Project 271, Final Report, April 1987, Chapter 2.)

Sampling from a steam line provides a further challenge because of the complex character of steam. By combining several isokinetic sampling nozzles in a primary steam line, one can obtain desirable sample line gas and liquid velocities. Because the sample line usually contains two-phase flow, due to condensing of the sample, the liquid and gas velocities constantly change along the sample line length, although the mass flow rate stays constant.

Steam and water samples taken from a power plant system are still quite hot and at high pressure, much too hot and at much too high a pressure to admit to most analysis instrumentation. Therefore, it is necessary to condense and cool a steam sample, and to cool a water sample, and then to reduce the pressure of the sample to near ambient level so the sample can be introduced to instrumentation at suitable conditions for analysis. Condensing and cooling is necessary before pressure reduction because steam would super heat and water would flash if the pressure was reduced before condensing and cooling.

One known system for conditioning a sample is the applicant's manually controlled, single-line sample panel for conditioning steam and water samples. This manually operated device includes a cooler for condensing and cooling the sample, and a pressure reducer comprising either a needle valve or applicant's variable pressure reducing element (VREL®). The VREL, used to reduce the pressure and to control the flow of a high pressure liquid sample, is a rod-in-tube device. The pressure of the incoming sample is reduced as the liquid is forced to travel through the narrow annular gap between a stepped rod and the inner diameter of the tube. The pressure drop through the VREL is a function of the length of the rod which is inserted into the tube. The flow through the VREL can be adjusted by manually changing the position of the rod in the tube. The manually operated sample panel provides for sample outlet to either analyzing instruments or for a grab sample or both.

The primary drawback of applicant's single line sample conditioning panel is that it must be manually operated and controlled. The steam cycle in a power plant is very dynamic, especially during start-up, so the device must be periodically, and at times continuously monitored and adjusted by an operator. Also, crud build-up in the sample line, cooler and VREL requires periodic manual adjustment of the VREL and cooling water flow.

U.S. Pat. No. 4,978,506 to Calderwood discloses a system for monitoring corrosive elements in the primary and secondary fluid systems of a nuclear power plant. The system includes elements for conditioning the sample for analysis. In the system disclosed by Calderwood, a sample is removed from the steam system by an isokinetic nozzle (reference number 11) connected to a sample line (12) and an isolation valve (14). The sample pressure is reduced by a capillary pressure reducer (16). A cooler (18) reduces temperature of the sample from an operating range of about 500° F. to 600° F. down to about 100° F. Indicators are included in the sample line (12) for pressure (20), temperature (22), and flow rate (24). A throttle valve (26) controls sample flow rate.

The capillary tubing mentioned in Calderwood may provide good service provided that the source pressure doesn't change and that the tubing doesn't plug. One of the drawbacks of using capillary tubing to reduce pressure is that sizing of the tubes must be done by trial and error, and once the length is set, the flow rate is not adjustable. Since the capillary tube is a fixed element, any change in source pressure causes a change in pressure drop and flow rate. At start up and shut down, in particular, the flow rate at lower pressures will be insufficient to provide a contemporary sample. Probably the greatest difficulty with capillaries is that their small bore is easily plugged with a piece of scale or crud. Once plugged, the capillaries cannot be easily unplugged and the line must be shut down while the tubing is cleared or replaced.

The Calderwood patent further mentions, at column 8, lines 51–57, that sample runs can be controlled automatically by a programmable controller to, for example, set the throttle valve (26) to ensure a constant sample flow rate. However, neither the programmable controller nor a program logic are shown in the drawings or described in the specification. Also, due to fouling of the capillary tubing, the mere addition of a programmable controller to the Calderwood system would not ensure constant sample flow rate. The application of an automatic controller to a sample conditioning system is just not as easy or economical as Calderwood suggests, and, more importantly, such an automatic system is not disclosed in the Calderwood patent.

Other systems for sampling, monitoring or analyzing a power plant steam-water cycle are disclosed in U.S. Pat. No. 4,766,550 to Byers et al., U.S. Pat. No. 4,713,772 to Carlson, U.S. Pat. No. 4,472,354 to Passel et al., and U.S. Pat. Nos. 3,880,226 and 3,871,444 to Houser et al. As with the Calderwood patent, these other patents do not disclose a specific device or system for automatically condensing, cooling and de-pressurizing steam and water samples at a constant flow rate.

SUMMARY OF THE INVENTION

An automated sample conditioning system for conditioning and preparing steam and hot water samples for analysis is disclosed. The system disclosed herein is designed for automated flow control to maintain constant flow rate and velocity in the sample line under varying system pressures and other flow disturbances which are encountered in a typical sampling operation at a power plant steam system.

Constant sample flow rate and velocity are achieved by continuously monitoring flow rate of the sample as it flows through the conditioning system. Fluctuations in sample flow are immediately and automatically corrected by adjusting the pressure drop across a motorized pressure reducing device.

The automated sample conditioning system of the present invention operates throughout the entire cycle of operations in a power plant steam system, including start-up and shutdown procedures, based on sample pressure. The invention automatically starts up when system pressure reaches a preset level, and automatically shuts down when sample flow cannot be maintained at the selected flow rate even though the pressure reducing device is wide open. During normal operations the invention maintains constant sample flow rate within required ranges as specified by the operator. The invention monitors and also alarms excessive pressure, temperature and flow parameters.

Primary components of the system include significant improvements to the cooler and the variable pressure reducing element (VREL ®) employed in applicant's earlier, manually operated, single line conditioning system. In addition to structural and sealing improvements to the VREL itself, the pressure reducing means is motorized to control and adjust the device in response to continuously monitored pressure readings at the sample line to maintain constant sample flow rate. Monitoring devices and displays with setpoint alarms are provided for primary sample temperature, secondary sample temperature, cooling water inlet or outlet temperature and flow rate. Automatic sample shut off capability is provided to stop sample flow in the event any of the monitored conditions surpass preset limits. A local control analyzer automates operation of the sample conditioning panel and provides visual display and alarms of sample parameters for flow rate, pressure and temperature.

The invention further includes communications equipment for remote control capability of all sample line functions. By providing, for instance, a desk top "PC" computer, the control analyzers on a number of conditioning panels can be combined into a network by simply joining each with simple wiring such as telephone hook-up wires. The central "PC" computer acquires all information required and can control each remote unit.

The primary objects of the invention are therefore to provide an automated sample conditioning system for condensing, cooling and reducing pressure of high temperature and high pressure steam and hot water samples; to provide automated sampling of hot fluids at a constant flow rate and velocity at varying pressures and temperatures; to provide continuous monitoring of sample pressure; to provide automated adjustment of the pressure reducing means in response to fluctuations in flow rate downstream in the sample line, thereby maintaining a constant sample flow rate; to provide an automated system for unattended sampling in centralized and remote locations during all phases of a power plant steam cycle; to monitor and alarm critical sample parameters, including primary and secondary sample temperatures, cooling water inlet or outlet temperatures, and sample flow rate; to provide local and remote data acquisition, display and control of critical sample parameters; and, to improve sample accuracy in order to provide reliable chemical analysis representative of conditions in the power plant steam system.

Other objects and advantages of the invention will become apparent from the following description taken in connection with the accompanying drawings which set forth, by way of illustration and example, certain preferred embodiments of the invention.

BRIEF DESCRIPTION OF THE DRAWINGS

The drawings, which are a part of the specification and which present an exemplary embodiment of the present invention, include the following:

FIG. 3 is a front plan view of an improved variable pressure reducing element (VREL).

FIG. 3A shows the internal rods which fit within the variable pressure reducing element.

FIG. 4 is a cross section view of the seal assembly of the variable pressure reducing element.

DETAILED DESCRIPTION OF THE INVENTION

Figure 1:
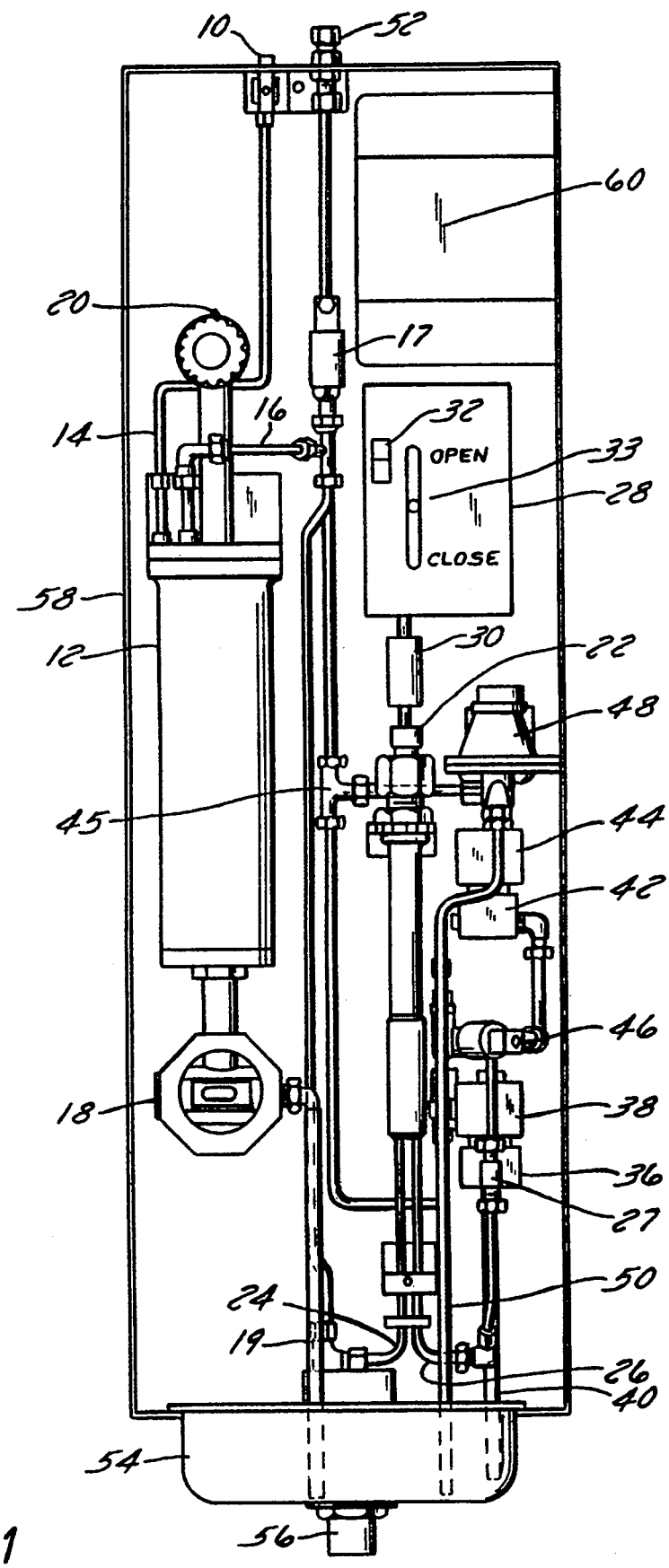
FIG. 1 is a front plan view of an automated sample conditioning module made in accordance with the principles of the invention disclosed herein.
Figure 2:
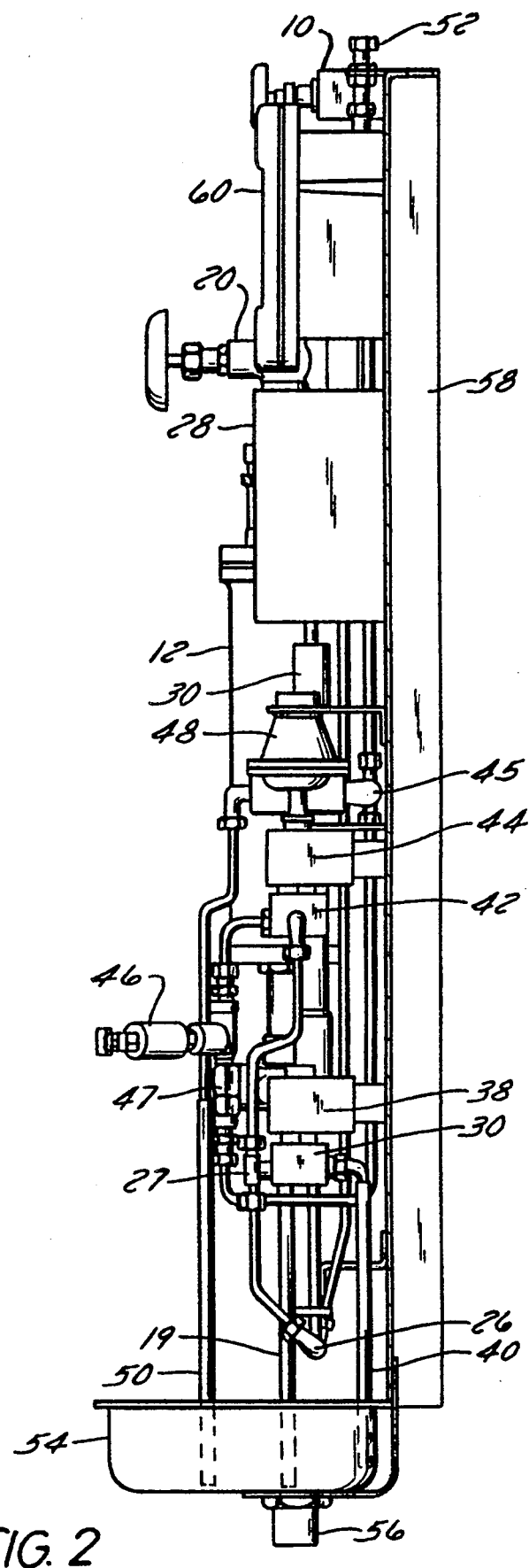
FIG. 2 is a side plan view of the automated sample conditioning panel.
Figure 5:
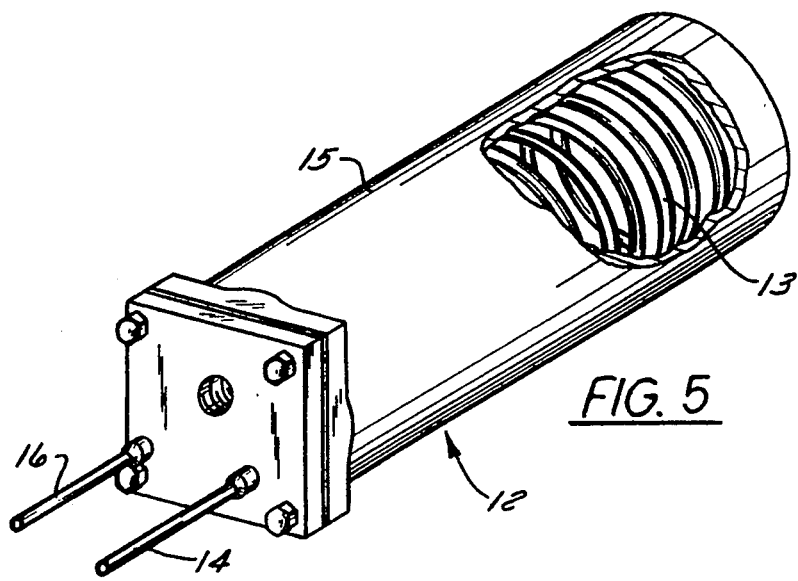
FIG. 5 is a perspective view, partially in section, of an improved sample condenser and cooler.
Figure 6:
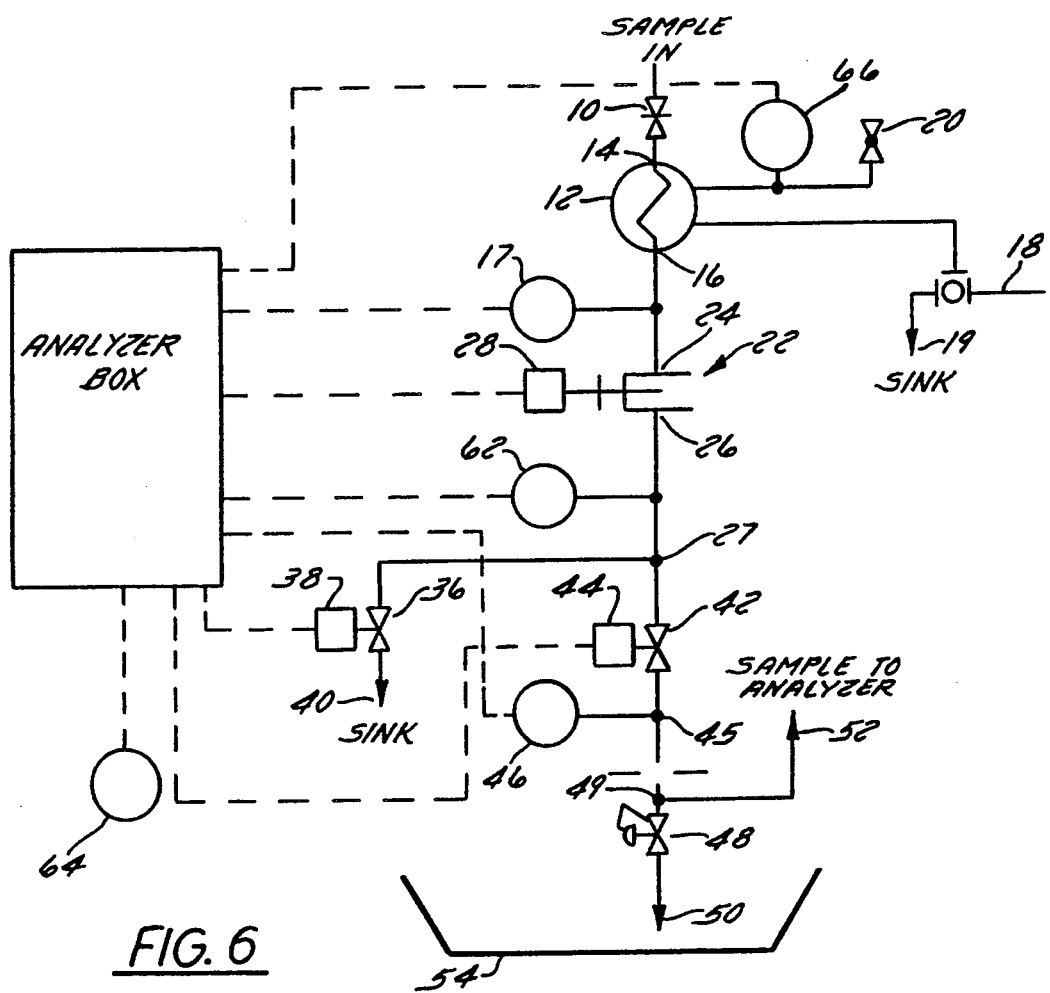
FIG. 6 is a process and instrumentation diagram of the automated sample conditioning system.

A steam or hot water sample taken from the steam-water system at a utility power plant enters the automated sample conditioning panel through the sample inlet valve 10. The sample flows into a sample cooler 12 through sample cooler inlet 14, where the sample flows through a cooling coil 13 within the cooler shell 15. The sample then exits the sample cooler 12 from sample cooler outlet 16. Cooling water enters the sample cooler 12 through cooling water inlet valve 18. The cooling water circulates within the shell among the sample line of cooling coils, thereby condensing and cooling a steam sample, or cooling a hot water sample, flowing through the sample line (i.e. through the cooling coil). Cooling water exits the sample cooler 12 through cooling water outlet valve 20.

The sample cooler 12 is a heavy duty, counterflow cooler for cooling steam or hot water up to 1000° F. and 5000 psig. The sample is cooled to a temperature of 120° F. or less. The sample line is wound into a cooling coil 13 which fits within a one-piece cylindrical shell 15 closed at one end by a plate welded to the bottom of the shell 15, and open on the other end with a mounting flange welded to the top of the shell 15. The shell 15 is removable for inspection or cleaning without disconnecting the sample line by a set of mounting bolts which fit through bolt holes in the mounting plate into threaded bolt holes in the flange. A gasket between the mounting plate and flange seals the cooling water within the shell 15.

Upon exiting the sample cooler 12, the sample travels past a first pressure transducer 17 where the primary sample pressure is continuously monitored. The sample continues to flow downward through the sample line to a means for reducing pressure of the sample, such as the variable pressure reducing element (VREL) 22 shown in FIGS. 1 and 3, or alternatively a needle valve. The variable pressure reducing element (VREL) 22 is used to reduce the pressure and control the flow of high pressure liquids, i.e. from as high as 5000 psi down to about 50 psi. A needle valve may instead be used for relatively lower pressure liquids, i.e., for reducing pressure from about 500 psi to 50 psi.

The VREL 22 is a rod-in-tube pressure reducing, flow control device. The VREL 22 is used to reduce very high pressure in the sample lines to a level at which the sample can be safely piped to an instrument or handled manually for a grab sample. The VREL 22 consists of two stainless steel tubes 72 and 73 joined to a larger tube or barrel 74. A pair of tapered rods 70 and 71 is inserted into the two tubes 72 and 73. The rods 70 and 71 are connected to a threaded ring 76 on a threaded guide screw 78 within the barrel 74. The sample enters the VREL at inlet 24. The pressure of the incoming sample is reduced as the liquid is forced to travel through the narrow annular gap between the outer diameter of the tapered rod 70 and the inner diameter of tube 72 and the gap between rod 71 and tube 73. The pressure drop through the VREL is a function of the length of the rod which is inserted into the tube, i.e. the pressure drop across the VREL is adjusted by changing the location of the rod within the tube. The sample exits the VREL 22 through outlet 26.

The flow through the VREL can be adjusted, even while the sample is flowing through it, by changing the position of the rods 70 and 71 in the tubes 72 and 73. By rotating the threaded guide screw 78 in one direction or the other, the threaded ring 76 moves the tapered rods 70 and 71 in or out of the tubes 72 and 73. The position of the rods 70 and 71 within the tubes 72 and 73, together with the tapered characteristic of the rods 70 and 71, control the pressure drop and flow rate of the sample through the VREL 22. In the event of a crud burst becoming lodged in the space between a rod and tube, the VREL 22 can be cleared by backing off the rods until the obstruction is blown free.

Looking at the VREL 22 seal 80 in FIG, 4, as the sample fluid flows through the VREL 22, the fluid exerts a frictional force against the inlet rod 70 in a direction toward the top end of the VREL 22 (i.e. toward the threaded ring 76), and a downward directed force against the outlet rod 71. Under optimal operating conditions, the forces approximately balance each other. This balanced arrangement facilitates lower mechanical stress on the valve for easier adjustment and promotes long valve life. As crud builds up, however, a large unbalanced force may develop tending to push the rods 70 and 71 and the guide screw 78 up and out of the VREL device 22. A shoulder 82 on the guide screw 78 holds it within a valve gland 84. A thrust washer 86 made of either PEEK ®, bronze, nylon, acetal or other suitable material, is placed between the shoulder 82 on the guide screw 78 and a ridge seat 85 of the gland 84. PEEK ®, available from LNP Engineering Plastics, Malvern, Pa., is a high lubricity (i.e. very smooth, low friction) material which permits the guide screw to turn fairly easily and causes negligible contamination to the sample.

The seal 80 is designed to facilitate easy rotation of the guide screw 78 with relatively low torques. A Teflon ® jacket 88 with a U-shaped cross section provides a seal around the outer diameter of the guide screw 78 and the inner diameter of the gland 84. An annular spring 90 presses the jacket 88 against the outer diameter of the guide screw 78 and the inner diameter of the gland 84. In addition, pressure "leaking" up through the device past the guide screw shoulder 82, thrust washer 86 and gland seat 85 further presses the jacket 88 against the outer diameter of the guide screw 78 and the inner diameter of the gland 84. The seal 80 is therefore essentially self-energized, that is, high pressure within the VREL 22 actually has the effect of improving the sealing effect of the jacket 88.

On the dry side of the jacket 88, a backup washer 92 also made of PEEK ® is placed against the upper side of the Teflon jacket 88. Under high pressure Teflon has a tendency to flow, so the PEEK ® backup washer prevents that phenomenon. The PEEK ® backup washer is very hard and has no gaps, and it also has a close fit around the outer diameter of the guide screw and inner diameter of the gland.

A bearing 94 centers the guide screw 78 in the gland 84. The bearing 94 has an annular flange 96 which fits on the upper surface 83 of the gland 84. The bearing 94, made of stainless steel, keeps the guide screw 78 centered in the event any type of lateral load is applied against it. A bearing washer 98 is placed over the bearing 94 to provide support over the entire top surface area of the bearing 94. In applications where very little lateral loading of the guide screw 78 is expected a bronze bushing may be used in place of the bearing and bearing washer. A nut 99 with a central opening for the guide screw 78 is threaded over the gland 84. Thus, the shoulder 82 of the guide screw 78 holds the guide screw 78 within the gland 84, and the nut 99 then holds the seal jacket 88 and spring 90, backup washer, bearing and bearing washer (or bushing) within the gland 84.

The position of the rods 70 and 71 within the tubes 72 and 73 of the VREL 22 is adjusted by the motor driver 28, which includes an alternating current (AC) motor attached to the VREL 22 by a motor-VREL connector 30. The connector 30 is a flexible coupling made from an aluminum rod machined into the form of a spring, primarily to accommodate slight misalignment of the axis of the motor driver 28 and the threaded guide screw 78 of the VREL 22. The motor is automatically controlled by the analyzer in control box 60 (discussed further below). A manual open/close toggle switch 32 on the motor driver box 28 permits an operator to manually override the control analyzer in control box 60 in order to open and close the VREL 22. The motor driver box 28 further has a position indicator 33 for visually displaying the relative position of the rods within the tubes.

The sample exits VREL 22 through VREL outlet 26 to pipe T-section 27, where the sample line T's off to blowdown valve 36, which is opened and closed by a blowdown solenoid 38. Opening the blowdown valve 36 provides blowdown of the sample line through blowdown line 40. During normal sampling operations, blowdown valve 36 is closed. The sample thus continues to flow past T-section 27, to sample valve 42, which is opened and closed by a sample solenoid 44.

Figure 7:
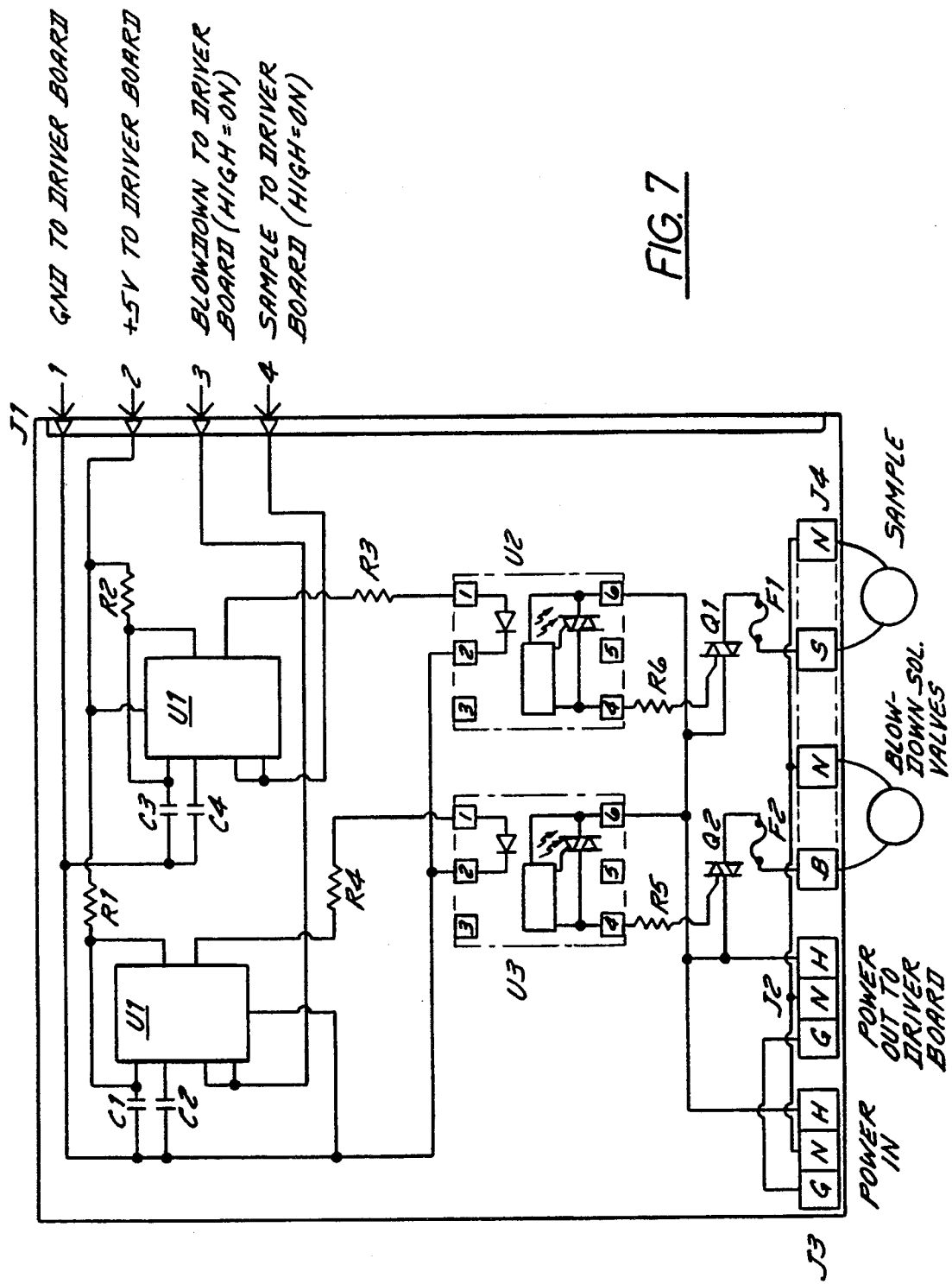
FIG. 7 is a schematic diagram of an auxiliary driver board of a solid state timer switch circuit to provide the inrush current for the solenoid valves.

The configuration of the sample conditioning panel shown in the drawings is constructed particularly for use in high pressure applications, i.e. 0 to 5000 psig. The sample valve 42 and solenoid 44 and the blowdown valve 36 and solenoid 38 utilize Aktomatic Solenoid Valves, Model SDW, available from Aktomatic Valve Company, Inc., Indianapolis, Ind., which require only about 0.22 to 0.30 amperes current to hold the plunger assembly. However, the inrush current to activate the valve plungers, which lasts for only onetenth second, is about 12 to 23 amps. The manufacturer ordinarily supplies a mercury relay switch with each solenoid valve to provide the inrush current, but the mercury relays are expensive and housed in a large enclosure. More importantly, most power plants prohibit any on-site mercury products. The sample conditioning panel of the present invention can be therefore provided with a timer switch circuit using solid state electronics, shown in FIG. 7, to provide the inrush current. The circuit plugs into the power supply board in the control analyzer box. Low pressure (0 to 500 psig) and medium pressure (0 to 2000 psig) configurations of the sample conditioning panel utilize Parker or ASCO solenoid valves which do not have high inrush currents and therefore do not require the additional timer switch circuit.

Following the sample valve 42, the sample then flows through the sample line past a second pressure transducer 46, where secondary sample pressure is monitored. Downstream from the second pressure transducer 46 the sample line has an orifice plate 47 of known diameter to meter the flow of the sample. The sample then travels downstream of the orifice plate 47 past T-section 45 to back pressure regulator/relief valve 48.

The back pressure regulator/relief valve 48 comprises a spring loaded diaphragm for moving a poppet in and out of an orifice in a casting for providing a fixed back pressure in the sample line of about 23 psi. When the sample flow is at 23 psi or lower, the poppet remains closed, in which case the sample flows only to the analyzer instrumentation 52. If the pressure is higher, then the poppet is pushed open to relieve excess pressure by sending excess flow to the grab sample line 50.

Upon going through the back pressure regulator/relief valve 48, the sample then travels down grab sample line 50, where it exits into a sink 54 and drain 56. An operator can then easily obtain a grab sample from grab sample line 50 at any time. For continuous analysis, the sample travels from T-section 45 through the sample line to analyzer connector 52, where the sample line is connected to associated analyzing instrumentation within the power plant.

Three temperature elements, 62, 64 and 66, are provided to monitor critical temperature parameters in the conditioning panel. The first temperature element 62 continuously monitors final sample temperature, i.e., after the sample has been cooled and depressurized. The second temperature element 64 monitors a temperature parameter on the sample conditioning panel desired by the user, such as at the cooling water inlet, secondary cooler temperature, or any other location the plant operator desires to monitor. The third temperature element 66 monitors cooling water exiting the sample cooler 12 at the cooling water outlet 20. Preliminary sample temperature may be monitored indirectly by monitoring the temperature of the cooling water inlet and cooling water outlet with temperature elements 64 and 66, respectively. High cooling water temperature indicates that the sample temperature is also extremely high due possibly to fouling or clogging of the sample line, or due to loss of cooling water, and may result in damage to the sampling instruments downstream from the conditioning panel. Each temperature element, 62, 64 and 66, comprises a temperature sensitive electronic chip soldered into the end of a signal wire and coated in silicone. Each temperature element is mounted with a copper clip onto the respective tubing or piping and wrapped with insulation. The copper clip provides good thermal conductivity to provide accurate reading of the actual temperature condition being monitored. Output of the electronic chip changes in direct relationship to the temperature being monitored, and the chip transmits an analog signal of the temperature to the control analyzer.

One of the primary objects of the invention is to provide a continuous sample at a constant flow rate and velocity at varying source pressures. This is achieved by continuously monitoring final sample flow rate and, in response to fluctuations in flow rate, automatically adjusting pressure drop across the motorized pressure reducing device. Final sample pressure is continuously monitored by the second pressure transducer 46 at a point in the sample line which is downstream from the pressure reducing device yet upstream from the orifice 47 and the back pressure regulator/relief valve 48. As mentioned above, the back pressure regulator/relief valve 48 regulates sample pressure to the analyzing instrumentation at a constant nominal pressure of 23 psi. The analyzer control box 60, which continuously receives a signal from the pressure readings monitored by the second pressure transducer 46, determines the flow rate in the sample line between the second pressure transducer 26 and the back pressure regulator/relief valve 48. Knowledge of the orifice plate 47 flow characteristics along with pressure values upstream and downstream of the orifice 47 permits accurate and consistent flow measurement.

The downstream pressure value is fixed at 23 psi by virtue of the back pressure regulator/relief valve 48. Applicant conducted lab tests of flow rates through an orifice of known diameter to determine the flow rate data versus varying upstream pressures. The flow rate at a set upstream pressure value is determined by measuring the total amount of flow over a known length of time. A series of tests by the applicant provided a set of pressure/flow rate data at varying upstream pressure values. The set of pressure/flow rate data from the lab tests is stored in the memory of the control analyzer 60. The control analyzer 60 compares the reading from the second pressure transducer 46 to the set of pressure/flow rate data stored in memory. The desired flow rate in the sample line can therefore be fixed and maintained on the basis of monitoring the upstream pressure value at the second pressure transducer 46, comparing upstream pressure value with a desired pressure value and corresponding flow rate, and adjusting the pressure reducing device 22 to maintain the upstream pressure value at a desired value.

If the pressure reading at the second pressure transducer 46 is too high, then flow rate is too high, and the control analyzer 60 automatically commands the motor driver 28 to adjust the VREL 22 or needle valve to a slightly more closed position, thereby increasing pressure drop across the pressure reducing device even further. Increasing the pressure drop across the pressure reducing device consequently reduces the pressure reading at the second pressure transducer 46, which in turn reduces flow rate to the desired level. Conversely, if the pressure reading at the second pressure transducer 46 is too low, which means that flow rate is too low, the control analyzer automatically opens slightly the motorized pressure reducing means to increase flow rate to the desired level.

The above-described means for calculating sample flow rate utilizes a back pressure regulator/relief valve 48 to provide a known downstream pressure value. The back pressure regulator/relief valve 48 is used on sample conditioning panels which deliver a sample to both analyzer instrumentation and grab samples. In the case where grab samples only are desired, the back pressure regulator/relief valve 48 may be omitted. In its place, a pipe of known diameter and length placed downstream from the orifice 47 provides a fixed pressure drop as fluid flows through the pipe. This fixed pressure drop of the pipe provides the downstream pressure value, and the flow rate is then calculated by the control analyzer 60 in the same method as described above.

The automated panel further provides for automatic sample on/off capability. Source pressure from the power plant steam system is monitored by the first pressure transducer 17, which is located downstream from the sample cooler 14 and upstream from the pressure reducing device 22. When the pressure at the first pressure transducer 17, reaches a preselected value which is continuously monitored by the control analyzer, the control analyzer essentially determines that the power plant boiler is on-line and that the sample conditioning panel should be activated to obtain samples for analysis. The first temperature element 62 and third temperature element 63 provide further information to verify that the sample conditioning panel is functioning properly and that samples may be obtained. When sample flow is opened, the second pressure transducer 46, control analyzer 60 and the motorized pressure reducing device 22 operate as described above to maintain constant sample flow rate.

When the power plant steam system shuts down, a reduction in sample pressure causes the pressure reducing device (i.e. the VREL or needle valve) to become fully opened. The position indicator 33 on the motor driver box 28 interrupts an optical limit switch upon crossing the optical path. The control analyzer 60 which recognizes that shutdown must occur immediately because the VREL 22 is wide open and cannot maintain the desired set point flow rate, shuts down the conditioning panel by closing all of the valves.

When the sample conditioning panel is activated, the blowdown solenoid 38 opens the blowdown valve 36, thereby providing for blowdown of the sample line and conditioning panel. The blowdown typically occurs for a preselected time period, as set via switches on the control analyzer.

Water chemistry analysis instrumentation downstream from the sample conditioning panel is typically made of plastic tubing and other materials which cannot tolerate high pressures or high temperatures. Analyzer instrumentation can typically handle a maximum pressure ranging from about 25–50 psi, depending on the particular equipment, and temperatures up to about 140° F. The control analyzer is therefore programmed to isolate the sample lines from analyzer instrumentation in the event of upset conditions, namely, high sample temperature which is continuously monitored by the first temperature element 62, or high sample pressure which is continuously monitored at the second pressure transducer 46, or high cooling water temperature which is continuously monitored by the third temperature element 66, or low sample flow rate (i.e. not adequate to maintain proper sample velocity) which is calculated by comparing the sample pressure monitored at the second pressure transducer 46 with the set of sample/flow rate data stored in the memory of the control analyzer. The control analyzer 60 is further programmed to provide an alarm warning to operators in the event that critical pressure and temperature limits are surpassed.

The combination of an automated sample valve and blowdown valve yields a fully unattended sampling system capable of automatic blowdown, start-up and shut down. The blowdown sequence occurs when the primary system pressure measured by the first pressure transducer 17 reaches a set-point and opens the blowdown valve 36 and pressure reducing device to blowdown the sample line for a set period of time. Automatic blowdown reduces crud build-up in the sample line and may improve the quality of the sample. Automatic start-up, in lieu of automatic blowdown, occurs when the first pressure transducer detects a build-up of pressure at the source. As the system pressure rises, the pressure reducing device 22 (the VREL or needle valve) are continually adjusted to maintain a constant sample flow rate at the desired level. Automatic start-up therefore permits the plant to begin representative sampling at the correct flow rate as soon as adequate pressure is available, and it enables the plant to closely monitor water chemistry at start-up since it has a significant effect on plant reliability. Automatic shutdown protects equipment and personnel from the hazards and potential damage caused by high temperatures and pressures. It also prevents non-representative sampling if the desired flow rate cannot be maintained.

The control analyzer 60 may be connected to a communications network to enable the user to remotely acquire data and to remotely monitor and control operations of the sample conditioning panel. A Texas Instruments RS 485 transceiver chip in the control analyzer provides a means for connecting the panel to a digital control system. Numerous panels may be connected to a single pair of twisted cables leading to a master control room in a safe area in the plant. Software in the control analyzer encodes analog signals from the temperature sensors and pressure transducers into a digital format and transmits the digitized information to the control room. Sample conditioning may therefore be conducted close to the source in a location which may be very hazardous to plant personnel and the operations may be completely controlled in a remote, safe area.

The system described above essentially includes all of the equipment necessary for an automated sample conditioning panel for use in a high pressure sampling operations for conditioning samples for both analyzer instrumentation and grab samples. The system described above may be modified, for example, for use in a low pressure sampling operation by substituting the VREL with a needle valve. As another example, the system may be modified to provide a grab sample only, in which case, the back pressure regulator/relief valve 48 is replaced with a pipe section of known diameter and length to provide a known pressure valve downstream of the orifice. The panel may be further modified by substituting the orifice meter and second pressure transducer with other means for measuring and monitoring flow rate, such as by a flow tube with a pressure transducer, turbine meter, vortex shedding meter, positive displacement meter, magnetic flow meter, optical counter and ultrasonic meter.

Therefore, specific details disclosed above are not to be interpreted as limiting, but merely as a basis of the claims and for teaching one skilled in the art to variously practice the present invention in any appropriately detailed manner. Changes may be made in the details of construction or operation of the invention without departing from the spirit of the invention, especially as defined in the following claims.

We claim as our invention the following:

1. A sample conditioning panel for automated conditioning of a high pressure fluid sample at relatively constant flow rate comprising:
   a motorized pressure reducing device for reducing pressure and controlling flow rate of the fluid sample;
   a pressure transducer for monitoring sample pressure downstream from the motorized pressure reducing device;
   an orifice downstream from the pressure transducer for metering the flow; and
   means for providing a known pressure value downstream from the orifice; and,
   automated control means for adjusting the motorized pressure response to changes in sample flow rate.

2. The sample conditioning panel according to claim 1, wherein the automated control means includes:
   a control analyzer for comparing a signal received from the pressure transducer with a stored set of pressure/flow rate data, and for transmitting a signal to adjust the motorized pressure reducing device in response to a change in the signal received from the pressure transducer.

3. The sample conditioning panel according to claim 1, wherein the means for providing a known downstream pressure value includes a fixed back pressure regulator/relief valve.

4. The sample conditioning panel according to claim 1, wherein the means for providing a known downstream pressure value includes a pipe of known length and diameter.

5. The sample conditioning panel according to claim 2, wherein the motorized pressure reducing device comprises a variable pressure reducing element.

6. The sample conditioning panel according to claim 5, wherein the variable pressure reducing element comprises a pair of tapered rods adjustably insertable within a complementary pair of tubes, thereby forming an annular gap between the outer diameter of the rods and the inner diameter of the tubes for fluid to flow therebetween.

7. The sample conditioning panel according to claim 6, further comprising a motor driver for adjusting the position of the rods within the tubes, an indicator for indicating the relative position of the rods within the tubes, a toggle switch for manually overriding the control analyzer to adjust the position of the rods, and a limit switch for transmitting a signal to the control analyzer in the event the adjustment of the rods reaches a set limit.

8. The sample conditioning panel according to claim 2, wherein the motorized pressure reducing device comprises a needle valve.

9. The sample conditioning panel according to claim 2, further comprising a sample valve for transmitting a fluid sample to analyzer instrumentation, with the sample valve being openable and closable by a sample solenoid in response to a signal from the control analyzer.

10. The sample conditioning panel according to claim 9, further comprising a blowdown valve for blowdown of the sample line with the blowdown valve being openable and closable by a blowdown solenoid in response to a signal from the control analyzer.

11. The sample conditioning panel according to claim 10, further comprising a primary sample pressure transducer for continuously monitoring sample pressure upstream from the motorized pressure reducing means.

12. The sample conditioning panel according to claim 11, further comprising a first temperature element for monitoring sample temperature downstream from the motorized pressure reducing device, a second temperature element for monitoring a second temperature parameter, and a third temperature element for monitoring temperature of a third temperature parameter.

13. The sample conditioning panel according to claim 12, wherein the control analyzer, in response to signals received from the pressure transducers and the temperature elements, transmits signals to the sample solenoid and the blowdown solenoid for actuating the sample valve and blowdown valve, respectively.

14. The sample conditioning panel according to claim 12, wherein the control analyzer converts analog signals received from the pressure transducers and temperature elements to digital signals for display and for transmission into a digital control system for remote control of the sample conditioning panel.

15. An automated sample conditioning module for conditioning steam and hot water samples for analysis at a relatively constant flow rate and velocity comprising:
   a sample cooler;
   an adjustable pressure reducing device downstream from the sample cooler;
   a motor connected to the pressure reducing device;

a pressure transducer for monitoring sample pressure downstream from the pressure reducing device;

an orifice downstream from the pressure transducer for metering sample flow;

means for providing a preset pressure value downstream from the orifice; and a control analyzer for calculating flow rate of the sample by comparing a sample pressure reading received from the pressure transducer with a stored set of pressure/flow rate data, and for transmitting a signal to the motor to adjust the pressure reducing device in response to changes in sample pressure monitored by the pressure transducer.

16. The automated sample conditioning module according to claim 15, wherein the means for providing a preset pressure value comprises a fixed back pressure regulator/relief valve.

17. The automated sample conditioning module according to claim 16, further comprising a sample line outlet for grab samples and an analyzer connection for delivering a sample to analyzer instrumentation.

18. The automated sample conditioning panel according to claim 15, wherein the means for providing a preset pressure value comprises a pipe section of predetermined length and diameter thereby providing a known pressure drop of fluid flowing through the pipe section.

19. The automated sample conditioning module according to claim 15, further comprising a blowdown valve openable and closable by a blowdown solenoid in response to signals received from the control analyzer, whereby opening of the blowdown valve permits blowdown of the sample line and conditioning module.

20. The automated sample conditioning module according to claim 19, further comprising a sample valve openable and closeable by a sample solenoid in response to signals received from the control analyzer whereby opening of the sample valve permits transmission of a sample to analyzer instrumentation for analysis.

21. The automated sample conditioning panel according to claim 20, further comprising a second pressure transducer upstream from the pressure reducing device.

22. The automated sample conditioning panel according to claim 20, further comprising a first temperature element for monitoring sample temperature downstream from the pressure reducing device, a second temperature element for monitoring a second temperature parameter, and a third temperature element for monitoring temperature of cooling water exiting the sample cooler.

23. The automated sample conditioning panel according to claim 22, wherein the control analyzer, in response to signals received from the pressure transducers and temperature elements, transmits signals to the sample solenoid and blowdown solenoid to activate the sample valve and blowdown valve, respectively.

24. The automated sample conditioning panel according to claim 23, wherein the control analyzer converts analog signals received from the pressure transducers and temperature elements to digital signals for display of temperatures and flow rate.

25. A method of conditioning a high pressure steam or hot water sample comprising:

cooling the sample;

reducing pressure of the sample;

monitoring the pressure of the sample after it has been copied and depressurized;

metering the sample flow past an orifice;

providing a set pressure value downstream from the orifice;

comparing the monitored pressure of the sample with a stored set of flow rate data; and, adjusting the pressure reduction of the sample in response to a change in the monitored pressure of the sample.

26. The method according to claim 25, further comprising regulating the back pressure of the sample.

27. The method according to claim 26, further comprising opening a blowdown valve to blow down the sample line.

28. The method according to claim 27, further comprising:

opening a sample valve; and transmitting the sample to analyzer instrumentation.

29. The method according to claim 25, further comprising monitoring the initial source pressure of the sample.

30. The method according to claim 29, further comprising:

monitoring initial temperature of the sample;

monitoring temperature of the sample after it has been cooled and depressurized; and monitoring temperature of cooling water used for cooling the sample.

31. The method according to claim 30, further comprising closing the blowdown valve and sample valve in the event the monitored pressures and temperatures exceed preset limits.

32. The method according to claim 31, further comprising converting analog signals of the monitored pressures and temperatures to digital signals and displaying the digital signals.

33. The method according to claim 32, further comprising controlling the method with a control analyzer connected locally to the sample line.

34. The method according to claim 33, further comprising controlling the method with a controller remotely from the sample line.

* * * * *